United States Patent
Groiso et al.

[11] Patent Number: 5,827,283
[45] Date of Patent: Oct. 27, 1998

[54] DEVICE AND METHOD FOR LOCATING TWO BONES INTO A DESIRED RELATIVE POSITION

[76] Inventors: Jorge Abel Groiso, Arenales 2245, 1° Piso; Horacio Fernando Miscione, Billinghurst 1676 P.B. "C", both of Buenos Aires; Ernesto Oscar Muñoz, Laprida 4125, Mar Del Plata, all of Argentina

[21] Appl. No.: 821,237

[22] Filed: Mar. 20, 1997

[30] Foreign Application Priority Data

Mar. 21, 1996 [AR] Argentina ................................. 335849

[51] Int. Cl.⁶ ................................................. A61B 17/60
[52] U.S. Cl. ................................................. 606/57; 606/54
[58] Field of Search ........................... 606/54, 55, 56, 606/59, 57, 58, 53

[56] References Cited

U.S. PATENT DOCUMENTS

| | | | |
|---|---|---|---|
| 4,628,922 | 12/1986 | Dewar | 606/54 |
| 4,768,524 | 9/1988 | Hardy | 606/54 |
| 4,889,111 | 12/1989 | Ben-Dov | 606/54 |
| 4,973,331 | 11/1990 | Pursley et al. | 606/54 |
| 5,207,676 | 5/1993 | Canadell et al. | 606/54 |
| 5,454,810 | 10/1995 | Pohl et al. | 606/59 |
| 5,630,815 | 5/1997 | Pohl et al. | 606/89 |

*Primary Examiner*—Guy V. Tucker
*Attorney, Agent, or Firm*—Londa and Traub LLP

[57] ABSTRACT

A device for locating in a desired position two or more bones or bone pieces that are in an undesired relative position, by bringing such pieces from the undesired position into the desired position, each piece having at least a pair of pins firmly fixed thereto, which pair of pins is, in turn, firmly retained in a retaining jaw member, the device comprising a straightforward and simple structure including two arms to be fixed to the jaw members and connected to arm driving motors for moving the arms along the three Cartesian axes, whereby the bones can be moved and located, or relocated, into the desired position under a controlled and programmed moving pattern, to achieve a non painful, accurate and exact correction of the bones position.

19 Claims, 2 Drawing Sheets

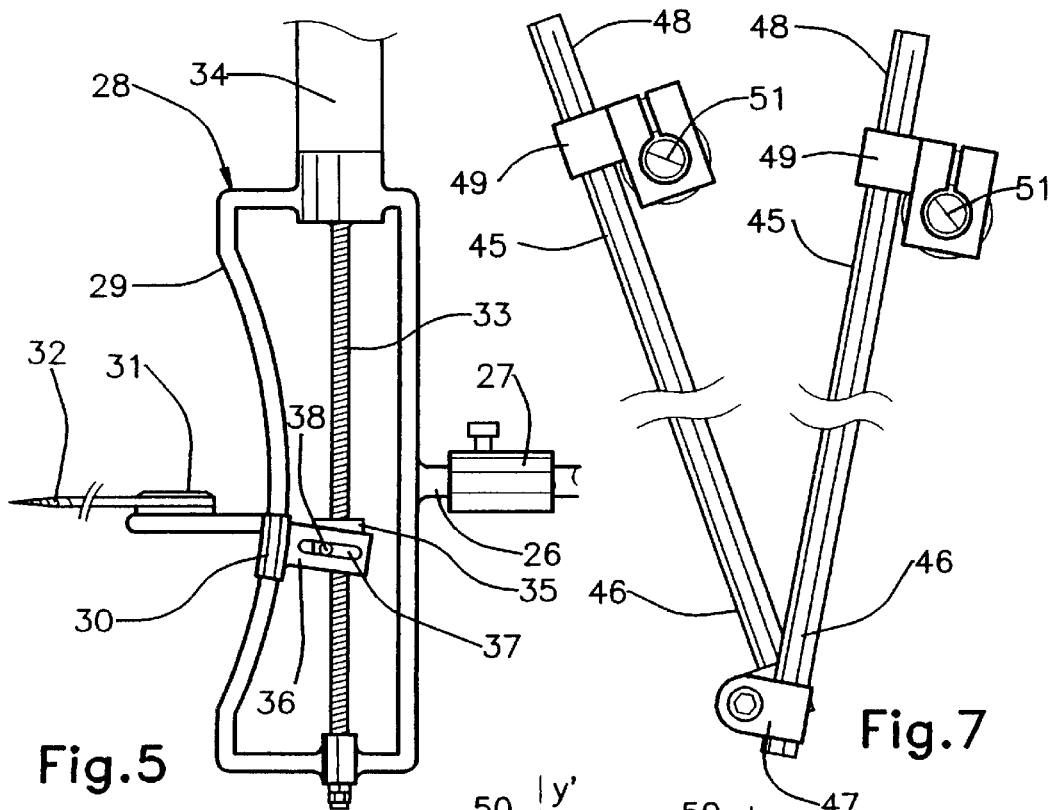
Fig.5
Fig.7
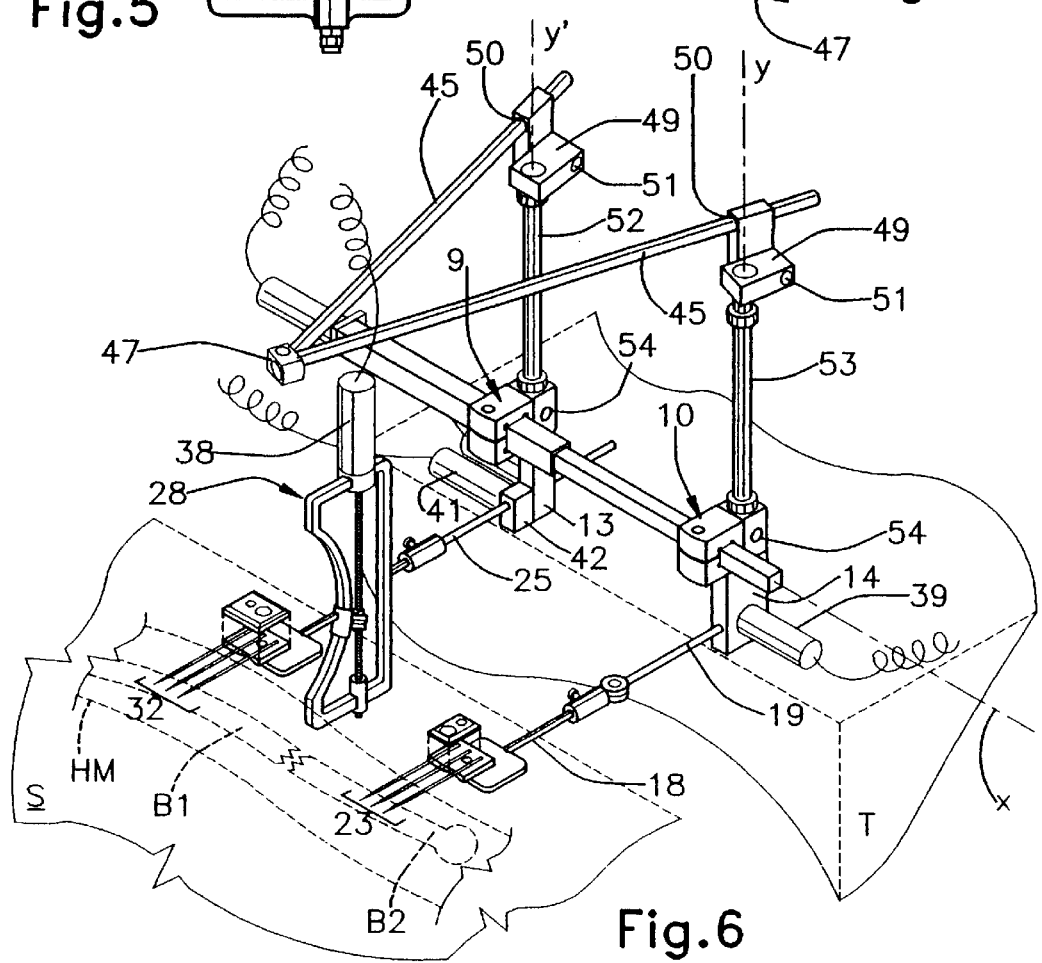
Fig.6

DEVICE AND METHOD FOR LOCATING TWO BONES INTO A DESIRED RELATIVE POSITION

BACKGROUND OF THE INVENTION

1. Field of the Invention

The present invention relates to the handling of two or more elongated pieces to bring them into a desired relative position and, more particularly, it refers to a device and method for relatively locating two pieces by bringing said pieces from a first undesired position into a second desired position wherein the pieces are preferably aligned into a longitudinal axis thereof.

Although along the present specification particular references will be made to the application of this invention to correcting the position of bones in pathologies like bones deviation, fractures, osteosynthesis and the like, the invention may be easily applied to the location or relocation of general elongated pieces which pieces must be spatially moved to bring them into a final and correct position, either by only one movement or a sequence of small and programmed movements carried out in a large period of time.

2. Description of the Prior Art

In one of the preferred applications of the invention such as the osteosynthesis, bone pieces must be correctly relocated in a patient that has suffered a fracture. In other applications, wherein the patient has a bone malformation for example, the bone or bones must be treated by making them longer. To carry out these treatments, modern techniques utilize fixing devices, such as external prop devices for helping to keep the bone parts or bones in a fixed and rigid position once the disorder has been corrected. Many prop or external fixing devices are well known, such as those known as "Ilizarov" and "Orthofix", which devices have multiple circular biomechanical structures by means of which all kind of spatial supporting can be achieved, such as in legs and arms of a human or animal body. The old techniques using plasters for treating fractures are being widely replaced by the use of these external fixing devices. The device and method of the present invention may be easily used in combination with any of these external fixing devices.

Many bone pathologies are treated nowadays by external fixing apparatii of the type known as monolateral fixing devices having two essential features, like stability in the plane wherein the fixing has been made and availability to make corrections in the bones and then fix the bones in position with high reliability. Most of the external movable monoplanar fixing devices differ, however, from the circular fixing devices in that the monoplanar devices must be manually operated by the physician through handles provided to be connected to pins already fixed to the bones. By firmly taking the handles, the doctor can move the bones along a range of movement which is restricted to the spatial movement availability depending on the type of fixing or prop apparatus. As it will be apparent to any one skilled in the art these movements are supported by the doctor arms thus transmitting to the bones undergoing correction many unnecessary, unstable and inaccurate movement changes.

The external fixing and prop devices basically comprise one or more bars connected to each other by pivoting connections including fastening screws for fixing the bars in a desired position to define a firm and rigid bar arrangement. These bars are in turn firmly fixed to a set of pins already fixed to the bones to be first located or relocated and then fixed in a rigid position. Upon a two-piece fracture these pins can be threaded in the corresponding two bone pieces. It is preferably that at least two or three pins are fixed to each bone or bone part to be handled. Each pin has a distal end fixed to the respective bone and a proximal end extending out the patient tissue so as to be accessible to the doctor. The proximal ends of the pins are then retained within an associated retaining jaw member to firmly clamp the pins together with the associated bone in a rigid configuration. Each jaw member is then connected to one handle which, as stated above, is taken by the doctor to manipulate the bones and change their relative position.

With an X-ray picture the physician makes an evaluation of the disorder, a fracture in a leg bone for example, and uses the handles to move the bone pieces and bring them to its original and correct position by placing the ends of the fracture in an abutting relationship. These movements are only guided by tact, the expertise, the orientation, and the visual observation. The doctor has no firm or fix points or frame to take as a reference for accurate and controlled manipulation of the bones. Once the doctor believes that the bone pieces are in the correct relative position, the fastening screws in the pivoting connections of the bars of the fixing device, which has already connected to the jaw members, are screwed to fix the bars into a rigid configuration to keep the relocated bones in the correct position. All these operations can not be carried out by only one person as long as when the bone pieces are in the correct position the doctor, who is manipulating the handles, can not let any handle free, for example to fix the screws, because the bones would come back to their incorrect position under the strong tensile forces of the leg muscles. Thus, generally a professional teem is necessary.

Therefore, when using the conventional and available fixing devices, an operation for relocating broken bones must be carried out in an operating room with the specialized personnel and surgical equipment with the patient being generally subject to unpleasant and painful situations.

In accordance with the foregoing it would be desirable to have a device and method for overcoming the above mentioned drawbacks associated wit the known fixing and prop apparatii, for accurately manipulating the bone pieces to locate or relocate the same in the exact desired position.

SUMMARY OF THE INVENTION

It is therefore an object of the present invention to provide a device for locating a relocating bone pieces in a desired relative position, in human beings and animals, wherein the device comprises a straightforward and firm structure comprising an assembly of rods, bars and arms, all movably connected to each other and capable of being operated by a person without the help of assistants, wherein once the bone pieces have been located or relocated in the desired position a conventional fixing apparatus may be firmly and accurately connected to the jaw members of the fixing apparatus. Once the fixing device is connected to the jaw members for keeping the bones in the desired position, the apparatus according to the present invention can be disconnected from the jaw members without running the risk of loosing the correct bones relative position. All these operations can be carried out in no more than thirty minutes without bringing the patient to an operation room, without the need of specialized additional equipment and personnel and without subjecting the patient to painful treatments. In addition, when large painful movements are necessary to treat the bones, the apparatus of the invention can be used to proceed with sequential and small programmed movements until reaching the entire relocation along several days, for example. Thus, a first day of a programmed treatment, the patient can be treated to just slightly bring the bones to a first position without subjecting the patient to an extremely large bones moving and a strong painful handling. In several following days the bones are again moved along small travels so as to make gradual corrections, that is in a step by step mode, until reaching the final desired position. This is a very important matter as long as the large movements nowadays carried out by manually moving the bones generally causes nervous and vascular damages while, with sequentially very small and controlled movements no damages are generated.

Another feature of the apparatus according to the invention is that the arms, bars and rods configuring the simple structure thereof are provided with controled driving means whereby the apparatus can be easily commanded by a computer program so as to obtain the exactly desired movements and/or sequence of movements of the bones along the three spatial Cartesian axes X, Y and Z. Thus, all the correcting movements can be performed softly, quickly simultaneously, and accurately.

It is still another object of the invention to provide a device for locating in a desired position two or more elongated pieces that are in an undesired relative position, by bringing such pieces from the undesired position into the desired position, each piece having at least a pair of pins firmly fixed thereto, which pair of pins is, in turn, firmly retained in a retaining jaw member, whereby each elongated piece is associated to one jaw member, the device comprising:

a support bar, at least two mounting blocks attached to the bar, the blocks moving along a longitudinal axis of the bar so as to move away from and against to each other, at least two arms, each arm being associated to one of the elongated pieces which are to be placed in the desired position, each arm having a distal end connected to one of the retaining jaw members fixed to the associated piece, and a proximal end connected to one of the blocks, first arm driving means connected to said blocks for rotatably moving each arm around a longitudinal axis thereof, second arm driving means connected to at least one block for axially moving the arm associated to said one block, third arm driving means connected to the blocks for rotatably moving the arms associated to said blocks around respective vertical axes of the blocks, bar driving means for causing the blocks to move along the longitudinal axis of the bar, and transverse rotary means in at least one of the arms for moving the associated retaining jaw member around a longitudinal axis of the elongated piece that is associated to the jaw member.

In a preferred structure of the device according to the invention, each block has a rotary hub having a vertical axle rotatably mounted in the hub, the vertical axle being connected to the third arm driving means.

In accordance with another embodiment of the invention two blocks are provided, and the third arm driving means comprise a pair of rods having respective distal ends connected by a hinge joint which joint defines an spatial hinge point above the jaw members, each rod having a proximal end connected to a connecting piece which, in turn, is connected to an upper end of each vertical axle, the connecting piece including an orifice passing through the connecting piece and receiving the associated rod slidably passing through the orifice, the connecting piece having retaining means to act in a retaining mode wherein the rod is firmly fixed into a desired position in the connecting piece, and a free mode, wherein the rod can freely move within the associated orifice of the connecting piece, each block further including axle locking means acting in a locking mode wherein the axle is locked against rotation relative to the block and a rotary mode wherein the axle can freely rotate within the block.

In still another embodiment of the invention, the third arm driving means comprises an electrical motor in each block, for rotating the vertical axle and its hub relative to the associated block.

It is still another object of the invention to provide a method for locating into a desired position two or more bones that are in an undesired relative position, in a human being or animal, by bringing such bones from the undesired position into the desired position, with the use of the above refered to device according to the invention, each bone including at least the pair of pins firmly fixed thereto, which pair of pins are, in turn, firmly retained in one retaining jaw member, whereby each bone is associated to one jaw member, the method comprising the steps of:

firmly connecting each distal end of the arms to one of the retaining jaw members;

actuating said block driving means to move said blocks along the support bar and axially locate each bone relative to each other;

actuating said second arm driving means for axially moving at least one of said arms so as to axially move one bone relative to the other;

actuating said third arm driving means for rotatably moving the arms around respective vertical axes of the blocks so as to rotate each bone around the vertical axis of the associated block, actuating said transverse rotary means for moving at least one of the bones around a longitudinal axis of the bone;

once the bones are in the desired position, fixing said retaining jaw members to at least one fixing apparatus to keep the bones in such desired position.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 5 is a side elevation view of the transverse rotary means connected to the distal end of another arm, for guiding another jaw member around the bone pieces shown in FIGS. 1 and 7;

FIG. 6 is a top perspective view of a second embodiment according to the invention, similar to FIG. 1, and, FIG. 7 is a top plan view of the pivoting rods configuring the third arm driving means of FIG. 6.

DESCRIPTION OF THE PREFERRED EMBODIMENTS

In the two embodiments described and shown, all the equivalent parts are indicated by the same reference numbers.

Figure 1:
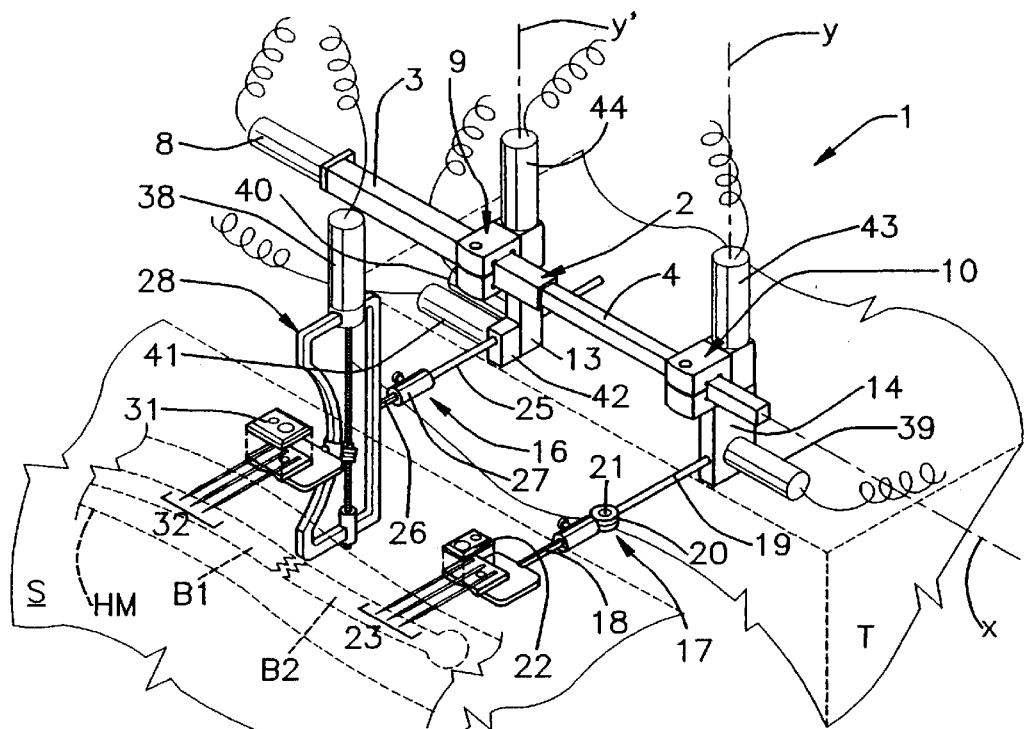
FIG. 1 is a top perspective view of a first embodiment according to the invention, showing in phantom lines a human member with a broken bone that is being relocated by the new apparatus.

Now referring in detail to the drawings FIG. 1 shows the device of the invention indicated by the generic reference number 1, which device comprises a structure capable of being firmly arranged in a table T, shown in phantom lines, to operate on a human member HM, such as an arm or a leg of a patient resting in a stretcher S, for locating or relocating bones or bone pieces B1, B2 into a desired relative position. The bones, the human member and the stretcher are also depicted in phantom lines.

The device structure comprises a contractile-extensible support bar 2 configured by two telescopic bar lengths, namely an outer bar length 3 and an inner bar length 4, both bar lengths being square-section tubular bars. As it is clearly shown in FIG. 2, a block-and-screw mechanism 5 comprising a threaded block 6 and an endless screw 7 is provided in a way that rotation of screw 7 causes block 6 to move longitudinally along the length of the screw. Since the screw is joined to bar length 3 and block 6 is fixed to bar length 4, bar lengths 3, 4 will move relative to each other so as to extend or retract the entire length of support bar 2. Endless screw 7 is arranged within bar lengths 3, 4 and it is connected to any suitable driving means such as an electrical motor 8 or any manually operated handle, not illustrated.

Figure 2:
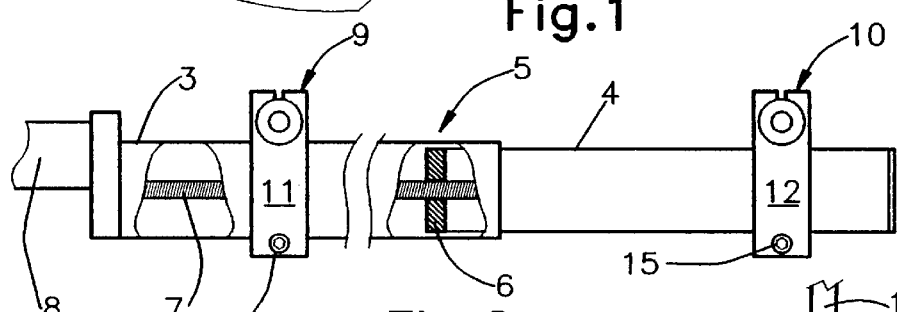
FIG. 2 is a partially sectional plan view of the support bar of the invention.
Figures 3, 4:
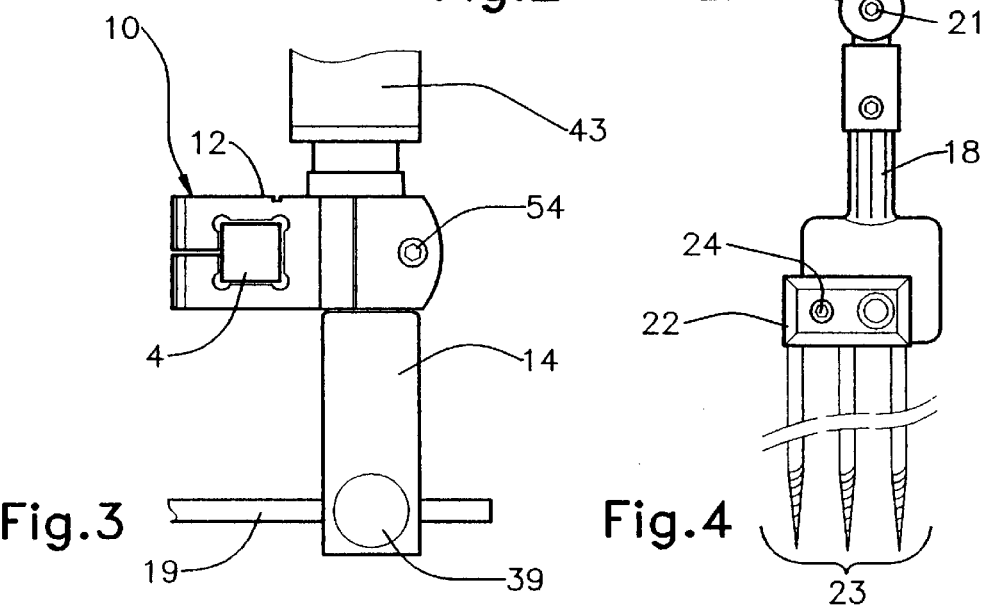
FIG. 3 is a side elevation view showing and end of the support bar, one mounting block and corresponding driving means.
FIG. 4 is a plan view of a retaining jaw member connected to a distal end of an arm of the apparatus of the invention, with the jaw member firmly retaining three pins of the type to be inserted into a bone piece.

As it is shown in FIGS. 1, 2, 3, a pair of mounting blocks 9, 10 are firmly attached to bar 2, particularly to bar lengths 3, 4. Thus, mounting block 9 is retained on bar length 3 and mounting block 10 is retained on bar length 4 whereby the extending and retracting relative movement between bar lengths 3, 4 will cause the blocks to move along a longitudinal axis X of bar 2 so that the blocks will move away from and against to each other. Each mounting block 9, 10, has a respective securing clamp portion 11, 12 and a respective transmission hub 13, 14.

Each clamp portion 11, 12 is releasably clamped to one of the bar lengths 3, 4, the respective clamp portion 11, 12, having fastening screws 15 to clamp and/or detach the clamp portion 11, 12, to and from the associated bar length 3, 4. Each hub 13, 14 preferably comprises a gear box rotatably connected to the associated block 9, 10.

For moving the bones in order to locate or relocate the same in the desired relative position, two arms 16, 17 are provided, each arm being connected to one of the mounting blocks.

Arm 17 is connected to hub 14 and comprises a distal portion 18 and a proximal portion or stem 19 connected through a hinge connection 20 having a fastener or screw 21 to fix both portions 18, 19 in the desired configuration. As it is better shown in FIG. 4, distal portion 18 is at one thereof connected to hinge connection 20 and at the other end is connected to a retaining jaw member 22 which firmly retains in a fixed relative position three pins 23. Pins 23 are first inserted into the bone piece B2 and extend out of human member HM so as to be accessible to the doctor. Once the pins are secured into the bone, jaw member 22 is fixed to the accessible ends of the pins and secured thereto by at least one screw 24. Pins 23 and jaw member 22 are parts of a conventional prop or fixing apparatus. That is, jaw member 22 is connected to arm 17 for locating or relocating bone piece B2 by means of the apparatus of the invention and, once the bone is at the desired position, such conventional fixing device is firmly connected to jaw member 22 to keep the pins and the bone in such obtained position.

Arm 16 comprises a proximal portion 25 connected to hub 13 and a distal portion 26, both portions being connected by a rigid connection 27. As it is shown in FIG. 5, distal portion 26 includes transverse rotary means comprising a frame 28 having a circular sector guide 29 along which a guide follower 30 is mounted, the guide follower being connected to an associated retaining jaw member 31 which, like in the case of jaw member 22, secures three pins 32. Like in FIG. 4, pins are shown out of the bones for clarity purposes but, when operating the apparatus of the invention, pins 32 are firmly fixed to bone piece B1, as shown in FIG. 1.

Frame 28 includes a worm 33 actuated by worm driving means comprising an electrical motor 34 and a threaded block 35 which is threadably slidably mounted on the worm so that, when worm 33 is rotated under the action of motor 34 block 35 moves up and down. Guide follower 30 has a tongue 36 including an elongated orifice 37. Block 35 has a transversely extending pin 38 which pin freely passes through orifice 37 so as to freely run along the orifice. When motor 34 is energized, worm screw 33 rotates and block 35 moves upwardly or downwardly depending on the sense of rotation of motor 34. When moving upwardly or downwardly, block 35 carries guide follower 30 also upwardly or downwardly along guide sector 29. In this way, bone B1, not illustrated in FIG. 5, will be moved around an axis (not illustrated) passing by the center of a virtual circumference defined by guide sector 29.

For rotating arms 16, 17 around respective longitudinal axis thereof first driving means are connected to the respective hubs 13, 14. The first driving means comprises an electrical motor 39 connected to hub 14 and an electrical motor 40 connected to hub 13. Rotation to arms 16, 17 will be provided by motors 39, 40 through any conventional gear arrangement (not illustrated) located within hubs 13, 14.

One of hubs 13, 14, and preferably hub 13, includes second arm driving means for moving the arm along a longitudinal axis of the arm and axially relative to block 9. Second driving means comprises an electrical motor 41 connected to an additional transmission hub, such as a gear box 42, through which arm 16 passes to be axially moved under the driving of motor 41.

At least one of the hubs, preferably hub 14, may be rotated around a vertical axis Y of the hub by third arm driving means comprising an electrical motor 43. Hub 13 can also be rotated in like manner, around a vertical axis Y' by an electrical motor 44.

With the provision of the first, second, third arm driving means 8, 39, 40, 41, 43, 44 and transverse rotary means 28 all the movements and positions in the space, as well as all their combinations can be achieved. This availability for all kinds of movements is advantageous for correcting bones deviations or malformations, for treating fractures, for elongating short malformed bones and for any other bone treating involving moving and positioning the bones into a desired configuration.

When using the device of the invention, a patient with a fracture is first treated to fix the pins to the bone pieces as usual. Once pins 23, 32 are firmly fixed to bone pieces B1, B2, jaw members 22, 31 are fixed to the pins already secured to the bones. Then, arms 16, 17 are fixed to the jaw members and the arms are moved in accordance with a moving pattern already programmed under observation basis, such as by means of X-rays. Once the bone pieces have been relocated to their original position by means of the device of the invention, a conventional fixing apparatus, such as that one known by the Trademark "Orthofix", is secured to the jaw members 22, 31 so as to keep the same in position and, hence, keep the bone pieces in the correct relative position.

When the patient is undergoing a bone treatment, such as orthopraxy, he already has a prop or a fixing apparatus attached to the arm or leg under correction. Therefore, the device of the invention is connected to the jaw members while these jaw members are still connected to the fixing device. Once arms 16, 17 are secured to the jaw members, the fixing device is removed to allow the device of the invention to adjust the position of the bone pieces. When the new position of the bones has been achieved, the fixing device is connected again to the jaw members and the fixing device is made rigid in this new position to keep the bone pieces in such a position.

In accordance with FIGS. 6, 7 a second embodiment is illustrated wherein the third arm driving means differ from the electrical motors 43, 44 of the embodiment depicted in FIG. 1. The rotary movement of arms 16, 17 around vertical axis Y, Y' is, in this embodiment, obtained by means of a compass-like system formed by a pair of rods 45. Rods have respective distal ends 46 connected by a hinge joint 47 which joint defines an spatial hinge point that is located above the jaw members, as it is clearly shown in FIG. 6.

Each rod has a proximal end 48, connected to a connecting piece 49 including an orifice 50, that receives the associated rod 45 slidably passing through the orifice, each connecting piece having retaining means, such as a screw 51 to act in a retaining mode and a free mode. In the retaining mode the rod is firmly fixed into a desired position in the connecting piece preventing the rod from sliding through orifice 50. In the free mode, screws 51 are released so that the rod can freely move within the associated orifice of the connecting piece.

Each connecting piece 49 is connected to an upper end of a respective vertical axle 52, 53 that has a lower portion rotatably connected to an associated block 9, 10 Each block includes axle locking means, such as a screw 54 acting in a locking mode and a free or rotary mode. In the locking mode, screws 54 are adjusted to lock the axle against rotation relative to the block while, in the rotary mode, screws 54 are released to allow the axle freely rotate within the block.

With the embodiment of FIG. 6, the apparatus is connected to the jaw members 22, 31 in like manner as it is described and illustrated in connection to the embodiment of FIG. 1. The difference with such first embodiment is that the rotation of the bone pieces B1, B2 around vertical axes Y, Y' is achieved without electrical motors but with the rotation of vertical axes 52, 53. To allow rotation of axles 52, 53 and hubs 13, 14 around axes Y, Y', screws 54 must be released, therefore, when motor 8 is actuated to extend or shorten bar 2, blocks 9, 10 will move relative to each other by moving away from or against to each other. Upon moving of blocks 9, 10, axles 52, 53 will rotate under the action of rods 45 through connecting pieces 49. For example, when blocks 9, 10 move away from each other the angle defined between rods 45 will increase, that is rods 45 will open and the inclination thereof regarding bar 2 will vary. This inclination will be accompanied by connection pieces 49 which, in turn, will make vertical axles 52, 53 rotate in a way that arms 16, 17 will rotate inwardly, that is towards each other, around axes Y, Y'.

In both described and illustrated embodiments, all the driving means, such as the first, second, third arm driving means 8, 39, 40, 41, 43 and 44 and transverse rotary means 34 may be commanded by computer a programmed unit so as to achieve accurate and precise movements.

Either with or without the use of a computer, with the device of the invention the painful and traumatic situations are overcome and no anesthesia is necessary. Neither an operation or surgical room is necessary, even when osteotomies are carried out.

All the bone corrections can be made during one or several operations as well as the several corrections can be sequentially performed along small correcting movements without the traumatic situations referred to above. This is a very important advantage for a bone elongation or in a pseudoarthrosis treatment, where the micropuncturing of the callus is a known problem.

Regarding the bone deviations, these deviations are commonly in all the space axes, the corrections, therefore, must be carried out in the three Cartesian axes X, Y, Z, and the inventive device is capable of carrying out these corrections in combined and simultaneous movements of the bones.

In an example of axial osteotomy the coordinate system of the proximal segment was defined by the orientation of the anatomic axis and an ideal bicondyle axis. Regarding the distal segment, the intersection between said anatomic axis and a predetermined transmallear axis was taken. The value of the clinic deformation resulted from the difference between the orientations of these two coordinate systems.

Thus, two parameters have been defined: spatial orientation and inclination degrees. The orientation was determined by the direction of the axis spatial projection while the inclination was determined through the relative axis of the horizontal lines.

The value of a deformity may be calculated as follows:

deformation value: angularity+translation

In this test the deformation in rotation was not considered because the deformation was monoaxial and the tests have been carried out with a monoplanar fixing device.

When hypothetical varus and valgus corrections were tested, that is deformations in the frontal radiological plane, the two center-axes corresponding to the bone pieces, proximal one and distal one, were defined to test the correction with the compass-like system of the invention. The apparatus was connected to the fixing device and several steps were defined to proceed with the planar movements. The angular movements were defined on the basis of the bone main axis and the central point of the angularity. The first correction was the horizontal translation, the second correction was the vertical translation, while the last corrections were the angular movements. Then, the same correction were carried out in a simultaneous mode, with all the movements carried out simultaneously, and the results obtained were satisfactory.

In accordance with the tests the following corrections were carried out:

1) Change in the translation axis

In a drawing, the distance in a horizontal deformation was measured. The overlapping degree was calculated from one end to the other in the bone pieces and the distance was compensated by a threaded rod, like a free elongating device. Then the vertical separation was calculated, that is the diastasis between one end and the other. The deformation was compensated by the bars and blocks of the present device.

2) Pure angular corrections

In an angular deformation the spatial hinge point 47 was located in the center of the angular deformation in an equidistant location. Then the relative position of the blocks was modified until the ideal desired angle between the bone pieces was reached.

3) Angular corrections with translation (combined movement)

It was demonstrated that when the eccentricity of the spatial hinge point exceeds the center of movement not only angular correction is achieved but also diastasis is obtained. When the hinge point does not exceeds the angle of the piece to be corrected, although axial correction is obtained, the same distance between the pieces decreases, moving in compression.

The axis of the pieces to be corrected must be defined and the points at the ends of the pieces define a line Z–Z' and a median line M of the line Z–Z' is drawn, directed to the concavity. A goniometer is located in a predetermined point to take the measure of the angle between line Z–Z' and the main axis of the piece to be corrected. The goniometer is placed in coincidence with the main axis of the piece under correction and the measured angle is translated to the concavity. With the goniometer then located in the base of the angle a median line M' is determined and this median line M' is compared with the median line M. When both median lines cross to each other the center of the movement is determined. The hinge point 47 must be located in this center so as to obtain, with only one combined movement, a correction to a combined deformation.

4) Angular corrections in the lateral axis

In "antecurvatum" or "recurvatum" corrections the main axis of the pieces to be corrected were drawn in the sagittal plane. Another line passing through the pins in the bone pieces was drawn. The angles to be corrected were determined in the intersection of both straight lines.

While preferred embodiments of the present invention have been illustrated and described, it will be obvious to those skilled in the art that various changes and modifications may be made therein without departing from the scope of the invention as defined in the appended claims. The electrical motors may be replaced for example by manually operated handles, and the motors, when used, may be controlled by computers.

We claim:

1. A device for locating in a desired position two or more elongated pieces that are in an undesired relative position, by bringing such pieces from the undesired position into the desired position, each piece having at least a pair of pins firmly fixed thereto, which pair of pins is, in turn, firmly retainable in a retaining jaw member, whereby each elongated piece is, fixable to one jaw member, the device comprising:

a support bar, at least two mounting blocks attached to the bar, the blocks being movable along a longitudinal axis of the bar so as to be movable away from and towards each other, at least two arms, each of said arms being connectable to one of the elongated pieces which are to be placed in the desired position, each of said arms having a distal end connected to one of the retaining jaw members fixable to one of the pieces, and a proximal end connected to one of the blocks, first arm driving means connected to said blocks for rotatably moving each of said arms around a longitudinal axis thereof, second arm driving means connected to at least one block for axially moving the one of said arms connected to said one block, third arm driving means connected to the blocks for rotatably moving the arms connected to said blocks around respective vertical axes of the blocks, bar driving means for causing the blocks to move along the longitudinal axis of the bar, and transverse rotary means in at least one of the arms for moving the retaining jaw member connectable thereto around a longitudinal axis of the elongated piece fixable to the jaw member.

2. The device of claim 1, wherein each block has a rotary hub having a vertical axle rotatably mounted therein, the vertical axle being connected to the third arm driving means.

3. The device of claim 2, wherein two blocks are provided, the third arm driving means comprising a pair of rods having respective distal ends connected by a hinge joint, which joint defines a spatial hinge point above the jaw members, each rod having a proximal end connected to a connecting piece which, in turn, is connected to an upper end of each vertical axle, the connecting piece including an orifice passing through the connecting piece and receiving the rod slidably passing through the orifice, the connecting piece having retaining means to act in a retaining mode wherein the rod is firmly fixed into a desired position in the connecting piece, and a free mode, wherein the rod can freely move within the orifice of the connecting piece.

4. The device of claim 3, wherein each block includes axle locking means acting in a locking mode wherein the axle is locked against rotation relative to the block and a rotary mode wherein the axle can freely rotate within the block.

5. The device of claim 2, wherein the third arm driving means comprises an electrical motor in each block, for rotating the vertical axle and its rotary hub relative to the block.

6. The device of claim 2, wherein each rotary hub comprises a power transmission mechanism.

7. The device of claim 6, wherein the power transmission mechanism is a gear box.

8. The device of claim 6, wherein said first arm driving means comprise an electrical motor connected to each of the hubs of the blocks and to the power transmission mechanism of the hub for rotatably moving each arm around a longitudinal axis thereof.

9. The device of claim 6, wherein said second arm driving means comprise an electrical motor connected to the power transmission mechanism of the hub in said at least one block for axially moving the arm connected to said one block.

10. The device of claim 2, wherein the bar is an extensible bar comprising two telescopically arranged bar lengths, said bar driving means extending and shortening the bar by telescopically moving one length relative the other.

11. The device of claim 10, wherein the bar lengths are tubular bar lengths and a bar-extending mechanism comprising a threaded block and an endless screw is arranged within the tubular bar lengths, the screw being actuated by said bar driving means.

12. The device of claim 10, wherein each mounting block is firmly retained in a respective one of the bar lengths so that the blocks move away from and toward each other with the extending and shortening of the telescopic support bar.

13. The device of claim 12, wherein each mounting block has a securing clamp portion releasably clamped to one of the bar lengths, the clamp portion having fastening screws to clamp and/or detach the clamp portion from the bar length.

14. The device of claim 10, wherein the bar driving means comprises at least one electric motor.

15. The device of claim 10, wherein the bar driving means comprises a manually operated handle.

16. The device of claim 2, wherein the transverse rotary means comprises a frame having a circular sector guide along which a guide follower is mounted, the guide follower being connected to the retaining jaw member, the frame including a worm that is actuated by worm driving means and a threaded block being threadably slidably mounted on the worm so as to move up and down under worm rotation, the threaded block being connected to the guide follower to move the guide follower along the circular sector guide and around an axis parallel to the longitudinal axis of the support bar.

17. The device of claim 2, wherein the elongated pieces are broken parts of a bone from a human skeletal structure.

18. The device of claim 2, wherein each arm comprises a distal portion carrying the retaining jaw member connected thereto and a proximal stem connected to one of said blocks, the distal portion and the stem being connected by a hinge connection.

19. A method for locating into a desired position two or more bones that are in an undesired relative position, by bringing such bones from the undesired position into the desired position with the use of the device of claim 1, each bone including at least the pair of pins firmly fixed thereto, which pair of pins are, in turn, firmly retained in one retaining jaw member, whereby each bone is associated to one jaw member, the method comprising the steps of:

firmly connecting each distal end of the arms to one of the retaining jaw members;

actuating said block driving means to move said blocks along the support bar and axially locate each bone relative to each other;

actuating said second arm driving means for axially moving at least one of said arms so as to axially move one bone relative to the other;

actuating said third arm driving means for rotatably moving the arms around respective vertical axes of the blocks so as to rotate each bone around the vertical axis of the block connected to said bone;

actuating said transverse rotary means for moving at least one of the bones around a longitudinal axis of the bone;

once the bones are in the desired position, fixing said retaining jaw members to at least one fixing apparatus to keep the bones in such desired position.

* * * * *